United States Patent [19] [11] Patent Number: 4,857,572
Meier et al. [45] Date of Patent: Aug. 15, 1989

[54] SUBSTITUTED PHENOLS AS STABILIZERS

[75] Inventors: Hans-Rudolf Meier, Marly; Gerrit Knobloch, Arisdorf, both of Switzerland

[73] Assignee: Ciba-Geigy Corporation, Ardsley, N.Y.

[21] Appl. No.: 157,116

[22] Filed: Feb. 10, 1988

Related U.S. Application Data

[63] Continuation of Ser. No. 59,235, Jun. 8, 1987, abandoned, which is a continuation of Ser. No. 928,130, Nov. 7, 1986, abandoned.

[30] Foreign Application Priority Data

Nov. 13, 1985 [CH] Switzerland ............ 4871/85
Sep. 24, 1986 [CH] Switzerland ............ 3826/86

[51] Int. Cl.$^4$ ............ C08K 5/36; C07C 149/273; C10M 135/30
[52] U.S. Cl. ............ 524/289; 252/48.2; 252/48.6; 524/222; 524/331; 560/15; 560/61; 560/254; 564/154; 568/46; 568/50; 568/55
[58] Field of Search ............ 524/289, 222, 331; 560/15, 61, 254; 564/154; 568/50, 46, 55

[56] References Cited

U.S. PATENT DOCUMENTS

| | | | |
|---|---|---|---|
| 2,332,376 | 6/1943 | McCleary et al. | 568/39 |
| 3,060,121 | 10/1962 | Orloff | 252/48.2 |
| 3,114,713 | 12/1963 | Coffield | 252/48.2 |
| 3,227,667 | 1/1966 | Moffitt et al. | 524/394 |
| 3,227,677 | 1/1966 | Simpson | 524/330 |
| 3,250,712 | 0/0000 | Coffield | 252/48.2 |
| 3,504,012 | 3/1970 | Braus et al. | 524/330 |
| 3,590,085 | 6/1971 | Braus et al. | 524/330 |
| 3,637,863 | 1/1972 | Braus et al. | 524/330 |
| 3,660,352 | 5/1972 | Song | 524/330 |
| 3,699,152 | 10/1972 | Hechenbleikner et al. | 560/75 |
| 3,789,616 | 1/1974 | Hechenbleikner | 560/15 |
| 3,903,173 | 9/1975 | Eggenspenger et al. | 524/330 |
| 4,091,037 | 5/1978 | Arold | 568/51 |
| 4,108,831 | 8/1978 | Cottman | 524/330 |
| 4,284,790 | 8/1981 | Hinsken et al. | 524/330 |
| 4,356,616 | 11/1982 | Wedemeyer et al. | 568/50 |
| 4,759,862 | 7/1988 | Meier | 568/55 |

FOREIGN PATENT DOCUMENTS 165209 10/1985 European Pat. Off. .
1569743 4/1969 France .
1184533 3/1970 United Kingdom .

*Primary Examiner*—Veronica P. Hoke
*Attorney, Agent, or Firm*—Harry Falber; Luther A. R. Hall

[57] ABSTRACT

Novel compositions are described which contain an elastomer or a tackifying resin and at least one compound of formula I $$\underset{\underset{CH_2-S-R_2}{\big|}}{\overset{\overset{OH}{\big|}}{\underset{R_1}{\bigcirc}}} CH_2-S-R_2 \quad (I)$$

The symbols $R_1$ is alkyl or cycloalkyl, $R_2$ is alkyl, hydroxyalkyl, phenyl or benzyl, and $R_3$ is hydrogen or methyl with the proviso that, when $R_1$ is other than methyl, $R_3$ is methyl. Some of the compounds of formula I are novel and are suitable as stabilizers for lubricants.

The novel compositions are suitable for the preparation of films or adhesives.

13 Claims, No Drawings

SUBSTITUTED PHENOLS AS STABILIZERS

This is a continuation of application Ser. No. 059,235, filed June 8, 1987, now abandoned, which in turn is a continuation of application Ser. No. 928,130, filed on Nov. 7, 1986, now abandoned.

The present invention relates to compositions containing a substituted bis(alkylthiomethyl)phenol as stabiliser, as well as to novel bis(alkylthiomethyl)-phenols.

Phenols containing alkylthiomethyl are known as stabilisers. For example, U.S. Pat. No. 3,660,352 describes the use of 2,4,6-trialkyl-bis(3,5-alkylthiomethyl)-phenols as antioxidants in polymers and elastomers. Moreover, 2,6-bis(alkoxycarbonylalkylenethiomethyl)-4-alkylphenols are known from U.S. Pat. No. 3,227,677 as antioxidants for polyolefines.

According to British patent specification No. 1 184 533, 2,4-bis(alkylthiomethyl)-3,6-dialkylphenols can be employed as stabilisers for organic polymers and also for synthetic oils.

There still exists a need for effective stabilisers for materials which are sensitive to thermal, oxidative or light-induced degradation.

Accordingly, the present invention relates to a composition containing an elastomer or a tackifying resin and at least one compound of formula I

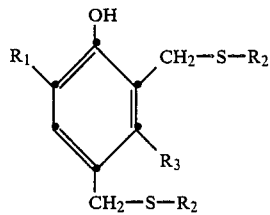

wherein $R_1$ is $C_1$–$C_8$alkyl or $C_5$–$C_{12}$cycloalkyl, the radicals $R_2$, each independently of the other, are $C_1$–$C_{18}$alkyl groups which are unsubstituted or substituted by 1 or 2 hydroxyl groups or by —OCO—$R_4$, —CO—OR$_5$ or —CO—NR$_5$R$_6$, or they are phenyl or benzyl, $R_3$ is hydrogen or methyl, with the proviso that, if $R_1$ is other than methyl, then $R_3$ is methyl, $R_4$ is $C_1$–$C_{17}$alkyl, $C_2$–$C_8$alkenyl or a radical of formula Ia

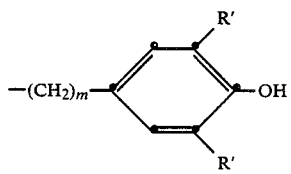

m is 0, 1 or 2, the radicals R', each independently of the other, have the meanings indicated for $R_1$, $R_5$ is $C_1$–$C_{20}$alkyl which may be interrupted by —O—, —S— or —NR'—, and $R_6$ is hydrogen or has one of the meanings indicated for $R_5$.

$R_1$ and R' as $C_1$–$C_8$alkyl are for example methyl, ethyl, n-propyl, isopropyl, n-butyl, sec-butyl, tert-butyl, n-pentyl, isopentyl, n-hexyl, 1,1-dimethylbutyl, n-heptyl, n-octyl or 2-ethylhexyl. Preferably, $R_1$ and R' are $C_1$–$C_4$alkyl, in particular methyl, ethyl, isopropyl or tert-butyl, most preferably methyl or tert-butyl.

$R_1$ and R' as $C_5$–$C_{12}$cycloalkyl are for example cyclopentyl, cyclohexyl, cycloheptyl, cyclooctyl or cyclododecyl. Preferably, $R_1$ and R' are $C_5$–$C_8$cycloalkyl, most preferably cyclohexyl.

$R_2$ as $C_1$–$C_{18}$alkyl is for example, in addition to the radicals indicated for $R_1$, also n-nonyl, n-decyl, 1,1,3,3-tetramethylbutyl, 1,1,3,3-tetramethylhexyl, n-undecyl, n-dodecyl, 1,1,3,3,5,5-hexamethylhexyl, n-tetradecyl, n-hexadecyl or n-octadecyl. Preferably, $R_2$ is $C_4$–$C_{18}$alkyl, most preferably $C_8$–$C_{18}$alkyl, e.g. n-octyl or n-dodecyl.

$R_2$ as $C_1$–$C_{18}$alkyl may be substituted by one or two hydroxyl groups. Examples of such radicals are 2-hydroxyethyl, 2-hydroxypropyl, 2-hydroxybutyl, 2-hydroxydodecyl, 2-hydroxyhexadecyl, 2-hydroxyoctadecyl or 2,3-dihydroxypropyl, with 2-hydroxyethyl being preferred.

$R_4$ as $C_1$–$C_{17}$alkyl is for example one of the radicals indicated for $R_2$ or methyl, with $C_1$–$C_{12}$alkyl, e.g. methyl, ethyl, n-propyl, isopropyl, n-butyl, tert-butyl, n-hexyl, n-octyl, 2-ethylhexyl or n-dodecyl, being preferred.

$R_4$ as $C_2$–$C_8$alkenyl is for example vinyl, allyl, methallyl, but-3-enyl, pent-4-enyl, hex-5-enyl, oct-7-enyl, dec-9-enyl or dodec-11-enyl, Preferably, $R_4$ is vinyl or allyl.

$R_4$ as a radical of formula Ia may be for example 4-hydroxy-3,5-dimethylphenyl, 4-hydroxy-3,5-di-tert-butylphenyl, 4-hydroxy-3,5-dimethylbenzyl, 4-hydroxy-3,5-di-tert-butylbenzyl or 4-hydroxy-3,5-dimethylphenylethyl, with 4-hydroxy-3,5-di-tert-butylbenzyl being preferred.

$R_5$ or $R_6$ as $C_1$–$C_{20}$alkyl is for example one of the radicals indicated for $R_2$ or methyl, octadecyl or eicosyl, with methyl, ethyl, n-hexyl, n-octyl or n-dodecyl being preferred.

$R_5$ or $R_6$ as $C_1$–$C_{20}$alkyl which is interrupted by —O—, —S— or —NR'— is for example 3-oxabutyl, 3-oxapentyl, 3,6-dioxaheptyl, 3,6,9-trioxadecyl, 3,6,9,12-tetraoxatridecyl, 3,6,9,12,15-pentaoxahexadecyl, 3,6,9,12,15,18-hexaoxanonadecyl, 3-thiabutyl, 3-azabutyl, 3-methyl-3-azapentyl, 3-ethyl-3-azapentyl, 3-methyl-3-aza-6-oxaheptyl, with 3-oxapentyl or 3-azabutyl being preferred.

Preferred compositions are those containing an elastomer and at least one compound of formula I.

Particularly preferred compositions are those containing an elastomer and at least one compound of formula I, wherein the radicals $R_2$, each independently of the other, are $C_2$–$C_{18}$alkyl groups which are unsubstituted or substituted by 1 or 2 hydroxyl groups or by —OCO—$R_4$, —CO—OR$_5$ or —CO—NR$_5$R$_6$, with $R_4$, $R_5$ and $R_6$ being as defined above.

More particulary preferred compositions are those which contain an elastomer or a tackifying resin and in which $R_1$ in formula I is $C_1$–$C_4$alkyl, preferably methyl or tert-butyl.

Further preferred compositions are those which contain an elastomer or a tackifying resin and in which $R_2$ in formula I is $C_4$–$C_{18}$alkyl, —CH$_2$CH$_2$—OH, —CH$_2$CH$_2$—O—CO—$R_4$, —CH$_2$—CO—$R_5$ or —CH$_2$CH$_2$—CO—$R_5$, with $R_4$ and $R_5$ being as defined above. A particularly preferred meaning of $R_2$ is $C_4$–$C_{18}$alkyl or —CH$_2$—COO—$R_6$, with $R_6$ being as defined above. Most preferably, $R_2$ is $C_4$–$C_{18}$alkyl.

Examples of representatives of compounds of formula I are the substances listed below:
2,4-bis(2'-hydroxyethylthiomethyl)-6-methylphenol,
2,4-bis(2',3'-dihydroxypropylthiomethyl)-3,6-dimethylphenol,
2,4-bis(2'-acetyloxyethylthiomethyl)-3,6-dimethylphenol,
2,4-bis(2'-n-decanoyloxyethylthiomethyl)-6-methylphenol,
2,4-bis(n-octylthiomethyl)-6-methylphenol,
2,4-bis(tert-octylthiomethyl)-6-methylphenol,[1]
[1]tert-octyl is 1,1,3,3-tetramethylbutyl
2,4-bis(tert-dodecylthiomethyl)-6-methylphenol,[2]
2,4-bis(benzylthiomethyl)-6-methylphenol,
2,4-bis(phenylthiomethyl)-3-methyl-6-tert-butylphenol,
2,4-bis(2'-ethylhexyloxycarbonylmethylthiomethyl)-6-methylphenol,
2,4-bis(n-octadecyloxycarbonylmethylthiomethyl)-3,6-dimethylphenol,
2,4-bis[2'-(2''-ethylhexyloxycarbonyl)ethylthiomethyl]-3-methyl-6-tert-butylphenol.
[2]tert-dodecyl is a mixture comprising 1,1,3,3,5,5-hexamethylhexyl and 1,1,4,6,6-pentamethylhept-4-yl Examples of materials which the compositions of the present invention may contain as elastomers are:

1. Polydienes, for example polybutadiene, polyisoprene or polychloroprene; block polymers, for example styrene/butadiene/styrene, styrene/isoprene/styrene or acrylonitrile/butadiene copolymers.

2. Copolymers of monoolefines and diolefines with each other or with other vinyl monomers, e.g. ethylene-/alkyl acrylate copolymers, ethylene/alkyl methacrylate copolymers, ethylene/vinyl acetate copolymers and terpolymers of ethylene with propylene and a diene, such as hexadiene, dicyclopentadiene or ethylidene-norbornene.

3. Halogen-containing polymers, e.g. polychloroprene, chlorinated rubbers, chlorinated or sulfochlorinated polyethylene, epichlorohydrin homo- and copolymers, chlorotrifluoroethylene copolymers, polymers from halogen-containing vinyl compounds, e.g. polyvinylidene chloride, polyvinylidene fluoride, as well as copolymers thereof, e.g. vinyl chloride/vinylidene chloride, vinyl chloride/vinyl acetate or vinylidene chloride/vinyl acetate.

4. Polyurethanes which are derived from polyethers, polyesters and polybutadiene with terminal hydroxyl groups on the one side and aliphatic or aromatic polyisocyanates on the other side, as well as precursors thereof.

5. Natural rubbers.

6. Mixtures (polyblends) of the above polymers.

7. Aqueous emulsions of natural or synthetic rubbers, e.g. natural rubber latex or latices of carboxylated styrene/butadiene copolymers.

These elastomers may be present in the form of latices and can be stabilised as such.

Preferred compositions are those containing as elastomer a polydiene such as polybutadiene rubber, a halogen-containing polymer such as polyvinylidene fluoride, or a polyurethane.

The compositions of the invention conveniently contain 0.01 to 10% by weight, preferably 0.05 to 5.0% by weight, of the stabiliser of formula I, based on the elastomer. Mixtures of stabilisers of formula I may also be employed.

Incorporation into the elastomers can be effected, for example, by blending in the substances of formula I and further optional additives by methods conventionally employed in the art, before or during moulding, or also by applying the dissolved or dispersed compounds to the polymer, with or without subsequent evaporation of the solvent. The compounds of formula I may also be added to the plastics to be stabilised in the form of a master batch which contains said compounds for example in a concentration of 2.5 to 25% by weight.

Examples of materials which the compositions of the present invention may contain as tackifying resins are:
natural colophonium resins (rosins) such as gum rosin, wood rosin, tall oil rosin
derivatives of colophonium resins, e.g. glycerol esters, pentaerythritol esters, each of which may be hydrogenated or non-hydrogenated, disproportionated or non-disproportionated
synthetic $C_5$- or $C_9$-hydrocarbon resins
indene resins, methylindene resins, coumarone-indene resins
terpene resins
methylstyrene resins
phenol resins
further tackifiers such as asphalt or bitumen
mixtures of the above resins
aqueous emulsions of the above resins.

Preferred compositions are those containing a synthetic $C_5$- or $C_9$-hydrocarbon resin, a colophonium resin or a derivative of colophonium resins.

The tackifying resinuous compositions conveniently contain 0.01 to 10% by weight, preferably 0.03 to 3.0% by weight, of the stabiliser of formula I, based on the tackifying resin. Mixtures of stabilisers of formula I may also be employed.

Incorporation of the compounds of formula I into the tackifying resins may be effected by methods conventionally employed in the art, before, during or after manufacture or modification.

The compositions of the invention can be used in a very wide range of forms, for example as films, filaments, ribbons, moulding compositions, profiles, or as binders for varnishes, adhesives or putties.

Some of the compounds of formula I are known. Those compounds of formula I which are novel likewise constitute an object of the present invention. Said novel compounds have the formula II.

Accordingly, the present invention also relates to compounds of formula II

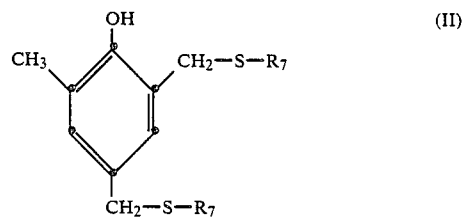

wherein the radicals $R_7$, each independently of the other, are $C_8$–$C_{18}$alkyl groups which are unsubstituted or substituted by 1 or 2 hydroxyl groups or by —O—CO—$R_4$, —CO—$OR_5$ or —CO—$NR_5R_6$, with $R_4$, $R_5$ and $R_6$ being as defined.

The exemplary and preferred meanings indicated above for $R_2$ in formula I also apply to $R_7$ in formula II. What is stated above with regard to $R_4$, $R_5$ and $R_6$ also applies to the symbols $R_4$, $R_5$ and $R_6$ in formula II.

Preferred compounds of formula II are those wherein the radicals $R_7$, each independently of the other, are unsubstituted $C_8$-$C_{18}$alkyl.

Particularly preferred compounds of formula II are those wherein the radicals $R_7$ are identical and are $C_8$-$C_{12}$alkyl.

The known and the novel compounds of formulae I and II are prepared by methods known per se, for example as described in British patent specification No. 1 184 533 and in U.S. Pat. No. 3,227,677. All starting materials are known compounds and can be prepared by known methods. Some of the starting materials are commercially available.

Further, the invention also relates to a process for the preparation of the compound of formula II, which comprises reacting 2,4-bis-(dimethylaminomethyl)-6-methylphenol with a mercaptan of the formula $R_7$-SH.

In addition to being suitable for the stabilisation of elastomers and of tackifying resins, the phenols of formula II of this invention are also suitable for the stabilisation of lubricants based on mineral oils or synthetic oils, in particular motor oils.

Suitable lubricants are known to the person skilled in the art and are described e.g. in "Schmiermittel Taschenbuch" (Handbook of Lubricants), Hüthig Verlag, Heidelberg, 1974.

Accordingly, the invention also relates to the use of compounds of formula II for stabilising lubricants against the action of oxygen, heat, light and energy-rich radiation.

The invention further relates to compositions containing a lubricant and at least one compound of formula II.

The phenols of formula II of this invention are conveniently added in a concentration of 0.01 to 10% by weight, based on the lubricant. It is preferred to employ 0.05 to 5.0% by weight, most preferably 0.1 to 2.0% by weight, of the phenols, based on the lubricant.

Mixtures of phenols of formula II may also be employed.

Lubricant formulations of this invention containing phenols of formula II may also contain other additives which are added to improve certain performance characteristics, e.g. further antioxidants, metal passivators, rust inhibitors, viscosity index improvers, pour-point depressors, dispersants/surfactants and anti-wear additives.

Examples of further additives with which, in lubricants, the phenols of formula II may be employed are:

1. ANTIOXIDANTS

1.1. Alkylated monophenols, e.g.

2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-isobutylphenol
2,6-dicyclopentyl-4-methylphenol
2-(α-methylcyclohexyl)-4,6-dimethylphenol
2,6-dioctadecyl-4-methylphenol
2,4,6-tricyclohexylphenol
2,6-di-tert-butyl-4-methoxymethylphenol

1.2. Alkylated hydroquinones, e.g.

2,6-di-tert-butyl-4-methoxyphenol
2,5-di-tert-butylhydroquinone
2,5-di-tert-amylhydroquinone
2,6-diphenyl-4-octadecyloxyphenol

1.3. Hydroxylated thiodiphenyl ethers, e.g.

2,2'-thiobis(6-tert-butyl-4-methylphenol)
2,2'-thiobis(4-octylphenol)
4,4'-thiobis(6-tert-butyl-3-methylphenol)
4,4'-thiobis(6-tert-butyl-2-methylphenol)

1.4. Alkylidenebisphenols, e.g.

2,2'-methylenebis(6-tert-butyl-4-methylphenol)
2,2'-methylenebis(6-tert-butyl-4-ethylphenol)
2,2'-methylenebis[4-methyl-6-(α-methylcyclohexyl)-phenol]
2,2'-methylenebis(4-methyl-6-cyclohexylphenol)
2,2'-methylenebis(6-nonyl-4-methylphenol)
2,2'-methylenebis(4,6-di-tert-butylphenol)
2,2'-ethylidenebis(4,6-di-tert-butylphenol)
2,2'-ethylidenebis(6-tert-butyl-4-isobutylphenol)
2,2'-methylenebis[6-(α-methylbenzyl)-4-nonylphenol]
2,2'-methylenebis[6-(α,α-dimethylbenzyl)-4-nonylphenol]
4,4'-methylenebis(2,6-di-tert-butylphenol)
4,4'-methylenebis(6-tert-butyl-2-methylphenol)
1,1-bis(5-tert-butyl-4-hydroxy-2-methylphenyl)butane
2,6-bis(3-tert-butyl-5-methyl-2-hydroxybenzyl)-4-methylphenol
1,1,3-tris(5-tert-butyl-4-hydroxy-2-methylphenyl)butane
1,1-bis(5-tert-butyl-4-hydroxy-2-methylphenyl)-3-n-dodecylmercaptobutane
ethylene glycol bis[3,3-bis(3'-tert-butyl-4'-hydroxyphenyl)butyrate]bis(3-tert-butyl-4-hydroxy-5-methylphenyl)dicyclopentadiene bis[2-(3'-tert-butyl-2'-hydroxy-5'-methylbenzyl)-6-tert-butyl-4-methylphenyl]terephthalate

1.5. Benzyl compounds, e.g.

1,3,5-tris(3,5-di-tert-butyl-4-hydroxybenzyl)-2,4,6-trimethylbenzene
bis(3,5-di-tert-butyl-4-hydroxybenzyl)sulfide
isooctyl 3,5-di-tert-butyl-4-hydroxybenzylmercaptoacetate
bis(4-tert-butyl-3-hydroxy-2,6-dimethylbenzyl)dithiolterephthalate
1,3,5-tris(3,5-di-tert-butyl-4-hydroxybenzyl)isocyanurate
1,3,5-tris(4-tert-butyl-3-hydroxy-2,6-dimethylbenzyl)isocyanurate
dioctadecyl 3,5-di-tert-butyl-4-hydroxybenzylphosphonate
calcium salt of monoethyl 3,5-di-tert-butyl-4-hydroxybenzylphosphonate

1.6. Acylaminophenols, e.g.

anilide of 4-hydroxylauric acid
anilide of 4-hydroxystearic acid
2,4-bis(octylmercapto)-6-(3,5-di-tert-butyl-4-hydroxyanilino)-s-triazine
octyl N-(3,5-di-tert-butyl-4-hydroxyphenyl)carbamate

1.7. Esters of β-(3,5-di-tert-butyl-4-hydroxyphenyl)propionic acid with mono- or polyhydric alcohols, e.g. with

| | |
|---|---|
| methanol | diethylene glycol |
| octadecanol | triethylene glycol |
| 1,6-hexanediol | pentaerythritol |
| neopentyl glycol | tris(hydroxyethyl) isocyanurate |
| thiodiethylene glycol | bis(hydroxyethyl)oxalic acid diamide |

1.8. Esters of β-(5-tert-butyl-4-hydroxy-3-methylphenyl)propionic acid

| | |
|---|---|
| with mono- or polyhydric alcohols, e.g. with | |
| methanol | diethylene glycol |
| octadecanol | triethylene glycol |
| 1,6-hexanediol | pentaerythritol |
| neopentyl glycol | tris(hydroxyethyl) isocyanurate |
| thiodiethylene glycol | bis(hydroxyethyl)oxalic acid diamide |

1.9. Amides of β-(3,5-di-tert-butyl-4-hydroxyphenyl)propionic acid, e.g.

N,N'-bis(3,5-di-tert-butyl-4-hydroxyphenylpropionyl)hexamethylenediamine
N,N'-bis(3,5-di-tert-butyl-4-hydroxyphenylpropionyl)trimethylenediamine
N,N'-bis(3,5-di-tert-butyl-4-hydroxyphenylpropionyl)hydrazine.

2. UV ABSORBERS AND LIGHT STABILISERS

2.1. 2-(2'-Hydroxyphenyl)benzotriazoles for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-(α,α-dimethylbenzyl) derivatives.

2.2. 2-Hydroxybenzophenones for example the 4-hydroxy, 4-methoxy, 4-octoxy, 4-decyloxy, 4-dodecyloxy, 4-benzyloxy, 4,2°,4'-trihydroxy and 2'-hydroxy-4,4'-dimethoxy derivatives.

2.3. Esters of substituted and unsubstituted benzoic acids for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines for example bis(2,2,6,6-tetramethylpiperidyl)sebacate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butane tetracarboxylate, 1,1'-(1,2-ethanediyl)-bis(3,3,5,5-tetramethylpiperazinone).

2.7. Oxalic acid diamides for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides and mixtures of o- and p-ethoxy-disubstituted oxanilides.

3. METAL PASSIVATORS for example N,N'-diphenyloxalic acid diamide, N-salicylal-N'-salicyloylhydrazine, N,N'-bis(salicyloyl)-hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide.

4. PHOSHITES AND PHOSPHONITES for example triphenyl phosphite, diphenylalkyl phosphites, phenyldialkyl phosphites, tris(nonylphenyl)-phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. PEROXIDE SCAVENGERS for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. POLYAMIDE STABILISERS for example copper salts in combination with iodides and/or phosphorus compounds and salts of divalent manganese.

7. BASIC CO-STABILISERS for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or tin pyrocatecholate.

8. NUCLEATING AGENTS for example 4-tert-butylbenzoic acid, adipic acid, diphenylacetic acid.

9. FILLERS AND REINFORCING AGENTS for example calcium carbonate, silicates, glass fibres, asbestos, talcum, kaolin, mica, barium sulfate, metal oxides and hydroxides, carbon black, graphite.

10. OTHER ADDITIVES for example plasticisers, lubricants, emulsifiers, pigments, fluorescent whitening agents, flame retardants, antistatic agents, blowing agents.

In practice, the compositions of the invention containing an elastomer or a tackifying resin and phenols of formula I may also contain further additives. Examples of such additives are:

1. ANTIOXIDANTS

Examples of antioxidants are to be found in the above list of additional additives for lubricants.

2. UV ABSORBERS AND LIGHT STABILISERS

2.1. 2-(2'-Hydroxyphenyl)benzotriazoles for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-(α,α-dimethylbenzyl) derivatives.

2.2. 2-Hydroxybenzophenones for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-phenyl-4-methylphenyl undecyl ketoneoxime, nickel complexes of 1-phenyl-4-lauroyl-5-hydroxypyrazole, with or without additional ligands.

2.6. Sterically hindered amines for example bis(2,2,6,6-tetramethylpiperidyl)sebacate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butane tetracarboxylate, 1,1'-(1,2-ethanediyl)-bis(3,3,5,5-tetramethylpiperazinone).

2.7. Oxalic acid diamides for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides and mixtures of o- and p-ethoxy-disubstituted oxanilides.

3. PHOSPHITES AND PHOSPHONITES for example triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, tristearyl sorbitol triphosphite, tetrakis(2,4-di-tert-butylphenyl)4,4'-biphenylene diphosphonite, 3,9-bis(2,4-di-tert-butylphenoxy)-2,4,8,10-tetraoxa-3,9-diphosphaspiro[5.5]undecane.

4. PEROXIDE SCAVENGERS for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

5. POLYAMIDE STABILISERS for example copper salts in combination with iodides and/or phosphorus compounds and salts of divalent manganese.

6. BASIC CO-STABILISERS for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or tin pyrocatecholate.

7. NUCLEATING AGENTS for example 4-tert-butylbenzoic acid, adipic acid, diphenylacetic acid.

8. FILLERS AND REINFORCING AGENTS for example calcium carbonate, silicates, glass fibres, asbestos, talcum, kaolin, mica, barium sulfate, metal oxides and hydroxides, carbon black, graphite.

9. OTHER ADDITIVES for example plasticisers, lubricants, emulsifiers, pigments, fluorescent whitening agents, flame retardants, antistatic agents, blowing agents, waxes, oils, organic solvents.

The invention is illustrated in more detail by the following Examples. In these Examples, in the remainder of the description and in the claims, parts and percentages are by weight.

PREPARATORY EXAMPLE

EXAMPLE 1

Preparation of 2,4-bis(n-octylthiomethyl)-6-methylphenol (compound 1)

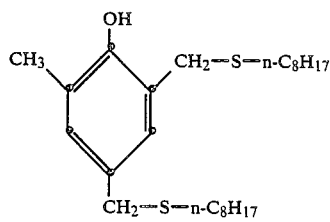

160.74 g (0.72 mole) of 2,4-bis(dimethylaminoethyl)-6-methylphenol and 210.65 g (1.44 moles) of n-octanethiol are mixed in an apparatus equipped with stirrer and multiple coil condenser for 36 hours at 150° C., with dimethylamine being continuously drawn off at 53.2 bar. 291.6 g (95%) of a yellow oil are obtained. Pure 2,4-bis(n-octylthiomethyl)-6-methylphenol is obtained in the form of a colourless oil by column chromatography of the crude product through silica gel.

Analysis values:

| calculated | 70.69% C | found | 70.85% C |
|---|---|---|---|
| | 10.44% H | | 10.42% H |
| | 15.09% S | | 15.11% S |

$^1$H-NMR (CDCl$_3$; 100 MHz; data in δ [ppm] based on TMS=0, s=singlet): characteristic signals for Ar-CH$_2$S at 3.77 (s) and 3.6 (s).

The following compounds of formula I are prepared in analogous manner:

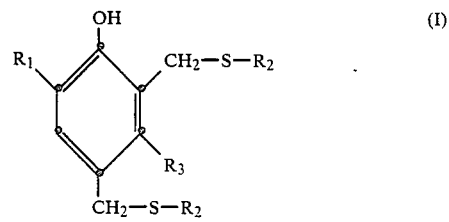

| Compound | R$_1$ | R$_2$ | R$_3$ | Physical data |
|---|---|---|---|---|
| compound 2 | CH$_3$ | n-C$_{12}$H$_{25}$ | H | m.p.: 28° C. |
| compound 3 | CH$_3$ | n-C$_{12}$H$_{25}$ | CH$_3$ | m.p.: 43° C. |
| compound 4 | C(CH$_3$)$_3$ | n-C$_{12}$H$_{25}$ | CH$_3$ | m.p.: 40° C. |
| compound 5 | CH$_3$ | n-C$_8$H$_{17}$ | CH$_3$ | liquid |
| compound 6 | CH$_3$ | (phenyl) | H | m.p.: 99°–100° C. |
| compound 7 | CH$_3$ | —CH$_2$—(phenyl) | H | liquid |
| compound 8 | CH$_3$ | —CH$_2$—COO—CH$_2$CH(CH$_2$CH$_3$)—(CH$_2$)$_3$—CH$_3$ | H | liquid |
| compound 9 | CH$_3$ | —CH$_2$CH$_2$—OH | H | liquid |
| compound 10 | CH$_3$ | —C(CH$_3$)$_2$—CH$_2$—C(CH$_3$)$_2$—CH$_2$—C(CH$_3$)$_3$ | H | liquid |
| compound 11 | CH$_3$ | —C(CH$_3$)$_2$—CH$_2$—C(CH$_3$)$_3$ | H | liquid |

APPLICATION EXAMPLES

Compounds 1 to 4 of Example 1 are tested for their stabilising action.

EXAMPLE 2

Stabilisation of polybutadiene rubber (oven ageing)

100 g of polybutadiene which has been prestabilised with 0.4% of 2,6-di-tert-butyl-p-cresol are blended homogeneously on a two-roll mill at 50° C. for 6 minutes with 0.25% of the stabilser to be tested. Samples having a thickness of 10 mm are pressed at 80° C. from the rolled sheet. A further sample is prepared in the same manner without a stabiliser.

The compositions of the invention are tested by subjecting the samples to thermal ageing in a circulating air oven at 80° C. The criterion for ascertaining the stability of the samples is the undesired gel content formed during oven ageing. The gel content is determined as follows:

1 gram of polybutadiene is dissolved overnight at room temperature in 100 ml of toluene. The solution is filtered through a glass filter funnel (pore size 00), and the filtered solution is evaporated to dryness.

The gel content is calculated using the following formula $$\text{gel} = \frac{E - A}{E} \times 100 \, (\%)$$

$E$ = weight-in quantity (1 gram)
$A$ = weight of the residue after evaporation

The gel content increases rapidly after an induction period. The time in which a sample exhibits a gel content of 2% is taken as the arbitrary definition of the induction period. In order to measure this induction period, the gel content is determined periodically.

The results are shown in Table 1.

TABLE 1

| Stabiliser | Induction time (in days) until the gel content is 2% |
| --- | --- |
| none | 21 |
| compound 2 | 77 |
| compound 3 | 84 |
| compound 4 | 56 |

EXAMPLE 3

Stabilisation of polybutadiene rubber (Brabender)

100 parts of polybutadiene which has been prestabilised with 0.4% of 2,6-di-tert-butyl-p-cresol are kneaded in a Brabender plastograph at 160° and 60 rpm for 30 minutes with 0.25% of the stabiliser to be tested. The induction time is measured from the flow of the torque, i.e. the kneading time in minutes until the increase in torque after the minimum torque is 100 mp.

The results are shown in Table 2.

TABLE 2

| Stabiliser | Induction time (in minutes) |
| --- | --- |
| none | 8 |
| compound 1 | >30 |
| compound 2 | 23 |
| compound 3 | 23.5 |
| compound 4 | 26 |

EXAMPLE 4

TFOUT test (Thin-film oxygen uptake test)

This test is a modified version of the rotary bomb oxidation test for mineral oils (ASTM D 2272). There is an exact description of the TFOUT test in C. S. Ku and S. M. Hsu, A Thin-Film Oxygen Uptake Test for the Evaluation of Automotive Crankcase Lubricants, Lubrication Engineering, Vol. 40 (2), pp. 75–83, (1984). The test oil is a motor oil based on mineral oil. The motor oil contains half of the customary amount of zinc dithiophosphate (0.75%; zinc content 0.06%, based on the motor oil); this change is made so that a potential effect of the stabiliser to be tested can be shown.

Compound 1 of Example 1 is tested in the above-described motor oil in the presence of 2% of water and in the presence of a liquid oxidated, nitrated fraction of a petrol as catalyst (4% concentration) and a liquid metal naphthenate as further catalyst (4% concentration; water and the two liquid catalysts were delivered with a certificate of analysis under Standard Reference Material No. 1817 of the National Bureau of Standards (NBS). The test is complete when there is a marked dip in the pressure/time diagram. The results shown in the Table below indicate the time (in minutes) until there is a dip in the pressure/time diagram.

Long periods of time correspond to good stabiliser activity. Concentration of the stabiliser: 0.5%, based on the oil.

TABLE 3

| Stabiliser | Time (in minutes) until marked drop in pressure |
| --- | --- |
| none | 85 |
| compound 1 | 134 |

EXAMPLE 5

Stabilisation of a hydrogenated $C_5$-hydrocarbon resin (oven ageing)

50 g of resin which has been prestabilised with 0.15% of 2,6-di-tert-butyl-p-cresol are melted in a glass flask at 170° C., and, with stirring, 0.1% of compound 1 are mixed in over 15 minutes. The hot melt is then poured into aluminium dishes and petri dishes. The layer thickness of the congealed resinuous mass is about 15 mm in the alumium dishes and 1 mm in the petri dishes. The composition of the invention is tested by subjecting the samples (=resinous masses) to thermal ageing in a circulating air oven at 170° C. The criterion for ascertaining the stability of the samples is the undesired discolouration occurring during oven ageing. Discolouration is determined as follows:

(a) in the case of the 1 mm samples: Yellowness Index according to ASTDM 1925-70 and
(b) in the case of the 15 mm samples: Gardner colour value according to DIN 6161.

Higher values indicate greater discolouration (this applies to both the Yellowness Index and to the Gardner colour value).

The results are shown in Table 4.

TABLE 4

| | Yellowness Index after hours at 170° C. | | | Gardner colour value after hours at 170° C. | | |
| --- | --- | --- | --- | --- | --- | --- |
| Stabiliser | 0 | 12 | 30 | 0 | 12 | 30 |
| none | 3 | 86 | 126 | 1 | 5 | 9 |
| compound 1 | 3 | 6 | 12 | 1 | 1-2 | 3-4 |

What is claimed is:
1. A stabilized composition which comprises
(a) an elastomer or a tackifying resin, and
(b) a stabilizing amount of at least one compound of formula I

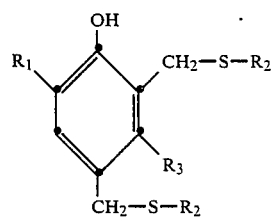

wherein $R_1$ is $C_1$–$C_4$-alkyl,
$R_2$, each independently of the other, are $C_1$–$C_{18}$-alkyl, —$CH_2COOR_5$ with $R_5$ being $C_1$–$C_{20}$-alkyl, —$CH_2CH_2OH$, phenyl or benzyl, and $R_3$ is hydrogen or methyl, with the proviso that, when $R_1$ is other than methyl, then $R_3$ is methyl.

2. A composition according to claim 1 wherein component (a) is an elastomer.

3. A composition according to claim 1 wherein $R_2$, each independently of the other, are $C_2$-$C_{18}$-alkyl, phenyl or benzyl.

4. A composition according to claim 2 wherein $R_1$ is methyl or tert-butyl.

5. A composition according to claim 1 wherein $R_2$ is $C_4$-$C_{18}$-alkyl, phenyl or benzyl.

6. A composition according to claim 5 wherein $R_2$ is $C_4$-$C_{18}$-alkyl.

7. A composition according to claim 1 wherein the elastomer is a polydiene, a halogen-containing polymer or a polyurethane.

8. A composition according to claim 1 which contains 0.05 to 5.0% by weight of component (b), based on the elastomer or tackifying resin of component (a).

9. A compound of formula II

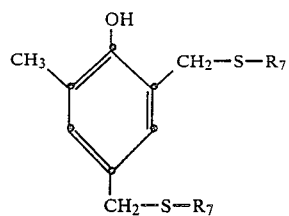

wherein $R_7$, each independently of the other, are $C_8$-$C_{18}$-alkyl, phenyl or benzyl.

10. A compound according to claim 9 wherein $R_7$, each independently of the other, are $C_8$-$C_{18}$-alkyl.

11. A compound of formula II

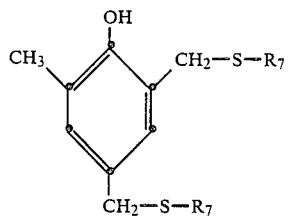

wherein the radicals $R_7$, each independently of the other, are $C_8$-$C_{18}$-alkyl —$CH_2COOR_5$ with $R_5$ being $C_1$-$C_{20}$-alkyl, —$CH_2CH_2OH$, phenyl or benzyl.

12. A method of stabilizing lubricants against the action of oxygen, heat and energy-rich radiation, which comprises
   incorporating therein a stabilizing amount of a compound according to claim 11.

13. A stabilized composition which comprises
   (a) a lubricant, and
   (b) a stabilizing amount of at least one compound according to claim 11.

* * * * *